(12) United States Patent
Gindelberger

(10) Patent No.: US 10,100,005 B1
(45) Date of Patent: Oct. 16, 2018

(54) MESALAZINE DERIVATIVES

(71) Applicant: Eclipse Therapeutics, LLC, Maryland Heights, MO (US)

(72) Inventor: David Gindelberger, St. Louis, MO (US)

(73) Assignee: Eclipse Therapeutics, LLC, Maryland Heights, MO (US)

( * ) Notice: Subject to any disclaimer, the term of this patent is extended or adjusted under 35 U.S.C. 154(b) by 0 days.

(21) Appl. No.: 15/848,956

(22) Filed: Dec. 20, 2017

Related U.S. Application Data

(60) Provisional application No. 62/587,667, filed on Nov. 17, 2017.

(51) Int. Cl.
    *C07C 251/28*    (2006.01)
    *A61K 31/606*   (2006.01)
    *A61P 1/00*      (2006.01)
    *A61P 1/04*      (2006.01)

(52) U.S. Cl.
    CPC .......... *C07C 251/28* (2013.01); *A61K 31/606* (2013.01); *A61P 1/00* (2018.01); *A61P 1/04* (2018.01)

(58) Field of Classification Search
    CPC . C07C 251/28; A61P 1/00; A61P 1/04; A61K 31/606
    See application file for complete search history.

(56) References Cited

PUBLICATIONS

Abdu-Allah (Medicinal Chemistry; 6(5), 306-315; 2016).*

* cited by examiner

*Primary Examiner* — Pancham Bakshi
(74) *Attorney, Agent, or Firm* — Husch Blackwell LLP

(57) ABSTRACT

Provided herein are compounds that are prodrugs for mesalazine. Generally, the compounds described herein correspond to a mesalazine molecule wherein the amino group is replaced by a novel protecting group. For example, in the compounds of Formula I described herein, the compound comprises a glyoxylate derivative moiety. In the compounds of Formula II described herein, the compound comprises a vanillin derivative moiety.

27 Claims, 2 Drawing Sheets

MESALAZINE DERIVATIVES

CROSS-REFERENCE TO RELATED APPLICATION

This application claims the benefit of U.S. Provisional Application No. 62/587,667, filed Nov. 17, 2017, which is hereby incorporated by reference in its entirety.

BACKGROUND

Mesalazine, also known as mesalamine or 5-aminosalicylic acid ("5-ASA") is an anti-inflammatory drug having the following structure.

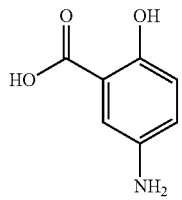

Mesalazine has proven to be an effective treatment for maintaining remission of Crohn's disease. It has also proven to be effective for treating the symptoms of inflammatory bowel disease ("IBS"), ulcerative colitis, and other conditions involving inflammation of the lower bowel.

Existing mesalazine formulations, however, exhibit a number of significant drawbacks. Although mesalazine can be administered orally as a treatment for Crohn's disease, it must be administered as a rectal suppository to be effective at treating conditions of the lower bowel. Existing mesalazine treatments require relatively large doses, and must be administered frequently to maintain effective control of inflammation.

It is therefore desirable to develop alternatives to existing mesalazine formulations that provide effective control of inflammation at lower doses of the active ingredient. It is also desirable to develop alternative active compounds that are easier and more economical to incorporate into stable pharmaceutical formulations.

SUMMARY

Provided herein is a compound of Formula I, or a salt thereof,

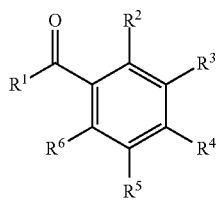

wherein
$R^1$ is selected from the group consisting of $-OR^9$ and $-N(R^{10}R^{11})$, wherein $R^9$, $R^{10}$, and $R^{11}$ are each independently selected from the group consisting of hydrogen and $C_1$-$C_6$ alkyl;
$R^2$ is selected from the group consisting of $-OR^{12}$ and $-N(R^{13}R^{14})$, wherein $R^{12}$, $R^{13}$, and $R^{14}$ are each independently selected from the group consisting of hydrogen and $C_1$-$C_6$ alkyl;
$R^3$ and $R^6$ are each independently selected from the group consisting of hydrogen, $C_1$-$C_6$ alkyl, $C_1$-$C_6$ alkoxy, carboxyl, halogen, and $CF_3$;
one of $R^4$ and $R^5$ is selected from the group consisting of hydrogen and $C_1$-$C_6$ alkyl, and the other of $R^4$ and $R^5$ is a moiety having the following structure:

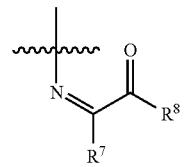

wherein $R^7$ is selected from the group consisting of hydrogen, $C_1$-$C_6$ alkyl, $C_1$-$C_6$ alkoxy, carboxyl, halogen, and $CF_3$;
and $R^8$ is selected from the group consisting of $-OR^{15}$ and $-N(R^{16}R^{17})$, wherein $R^{15}$, $R^{16}$, and $R^{17}$ are each independently selected from the group consisting of hydrogen and $C_1$-$C_6$ alkyl.

Also provided herein is a compound of Formula II, or a salt thereof,

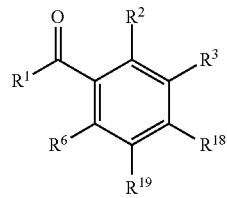

wherein
$R^1$ is selected from the group consisting of $-OR^9$ and $-N(R^{10}R^{11})$, wherein $R^9$, $R^{10}$, and $R^{11}$ are each independently selected from the group consisting of hydrogen and $C_1$-$C_6$ alkyl;
$R^2$ is selected from the group consisting of $-OR^{12}$ and $-N(R^{13}R^{14})$, wherein $R^{12}$, $R^{13}$, and $R^{14}$ are each independently selected from the group consisting of hydrogen and $C_1$-$C_6$ alkyl;
$R^3$ and $R^6$ are each independently selected from the group consisting of hydrogen, $C_1$-$C_6$ alkyl, $C_1$-$C_6$ alkoxy, carboxyl, halogen, and $CF_3$;
one of $R^{18}$ and $R^{19}$ is selected from the group consisting of hydrogen, $C_1$-$C_6$ alkyl, $C_1$-$C_6$ alkoxy, carboxyl, halogen, and $CF_3$, and the other of $R^{18}$ and $R^{19}$ is a moiety having the following structure:

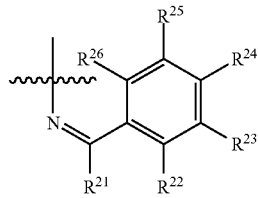

wherein
$R^{21}$, $R^{22}$, $R^{25}$, and $R^{26}$ are each independently selected from the group consisting of hydrogen, $C_1$-$C_6$ alkyl, $C_1$-$C_6$ alkoxy, carboxyl, halogen, and $CF_3$;

$R^{23}$ is selected from the group consisting —$OR^{27}$ and —$N(R^{28}R^{29})$, wherein $R^{27}$, $R^{28}$, and $R^{29}$ are each independently selected from the group consisting of hydrogen and $C_1$-$C_6$ alkyl; and $R^{24}$ is selected from the group consisting of —$OR^{30}$ and —$N(R^{31}R^{32})$, wherein $R^{30}$, $R^{31}$, and $R^{32}$ are each independently selected from the group consisting of hydrogen and $C_1$-$C_6$ alkyl.

Also provided herein is a pharmaceutical composition comprising a compound as provided herein (e.g., a compound of Formula I or Formula II).

Also provided herein is a method of treating an intestinal inflammatory disorder in a human, the method comprising administering a pharmaceutical composition as provided herein to a human having said intestinal inflammatory disorder.

DETAILED DESCRIPTION

Figure 1:
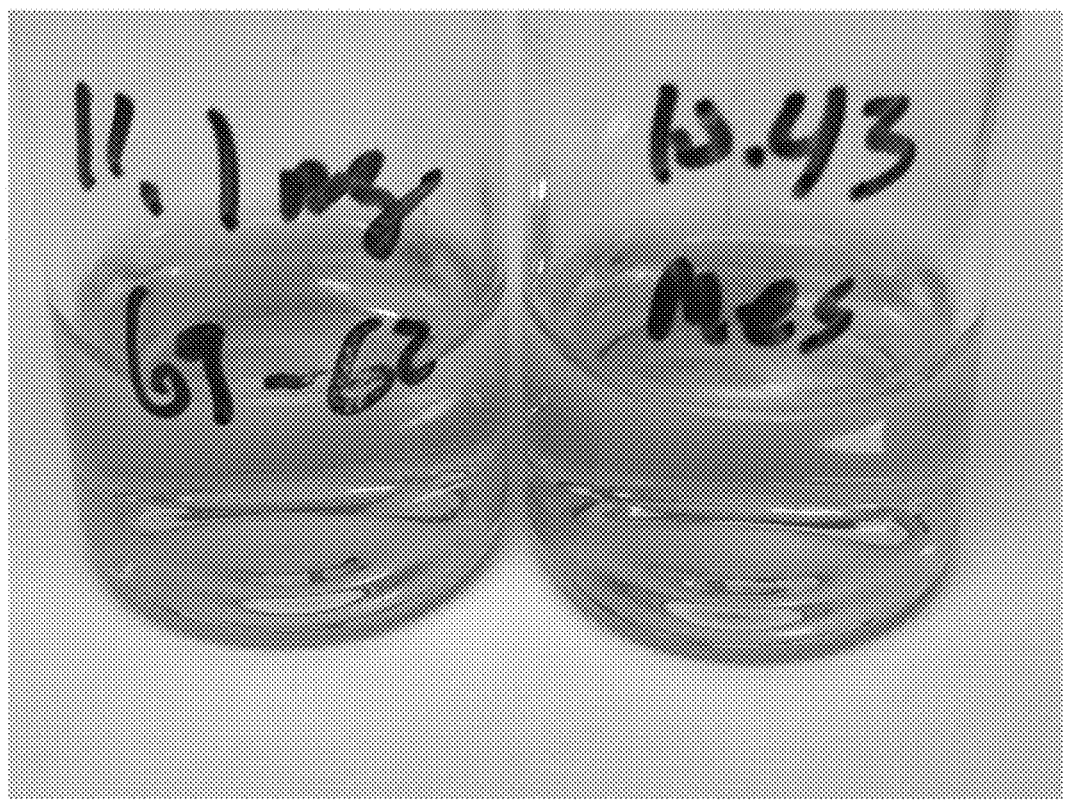
FIG. 1 is a photograph of vials containing 5-glyoxyliminosalicylic acid (left) and mesalazine (right), each dissolved in an aqueous sodium phosphate buffer as described in Example 11.

Provided herein are compounds that are prodrugs for mesalazine. Generally, the compounds described herein correspond to a mesalazine molecule wherein the $NH_2$ group is replaced by a novel protecting group. For example, in the compounds of Formula I described herein, the compound comprises a glyoxylate derivative moiety. In the compounds of Formula II described herein, the compound comprises a vanillin derivative moiety.

For example, provided herein is a compound of Formula I, or a salt thereof,

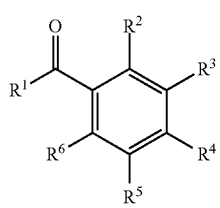

Formula I wherein
  $R^1$ is selected from the group consisting of —$OR^9$ and —$N(R^{10}R^{11})$, wherein $R^9$, $R^{10}$, and $R^{11}$ are each independently selected from the group consisting of hydrogen and $C_1$-$C_6$ alkyl;
  $R^2$ is selected from the group consisting of —$OR^{12}$ and —$N(R^{13}R^{14})$, wherein $R^{12}$, $R^{13}$, and $R^{14}$ are each independently selected from the group consisting of hydrogen and $C_1$-$C_6$ alkyl;
  $R^3$ and $R^6$ are each independently selected from the group consisting of hydrogen, $C_1$-$C_6$ alkyl, $C_1$-$C_6$ alkoxy, carboxyl, halogen, and $CF_3$;
  one of $R^4$ and $R^5$ is selected from the group consisting of hydrogen and $C_1$-$C_6$ alkyl, and the other of $R^4$ and $R^5$ is a moiety having the following structure:

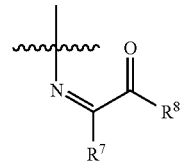

wherein $R^7$ is selected from the group consisting of hydrogen, $C_1$-$C_6$ alkyl, $C_1$-$C_6$ alkoxy, carboxyl, halogen, and $CF_3$;
  and $R^8$ is selected from the group consisting of —$OR^{15}$ and —$N(R^{16}R^{17})$, wherein $R^{15}$, $R^{16}$, and $R^{17}$ are each independently selected from the group consisting of hydrogen and $C_1$-$C_6$ alkyl.

For example, the compound of Formula I may be a compound of Formula Ia or a salt thereof,

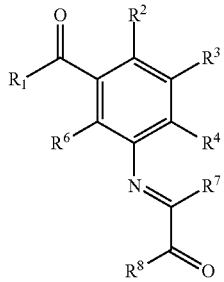

Formula Ia wherein
  $R^1$ is selected from the group consisting of —$OR^9$ and —$N(R^{10}R^{11})$, wherein $R^9$, $R^{10}$, and $R^{11}$ are each independently selected from the group consisting of hydrogen and $C_1$-$C_6$ alkyl;
  $R^2$ is selected from the group consisting of —$OR^{12}$ and —$N(R^{13}R^{14})$, wherein $R^{12}$, $R^{13}$, and $R^{14}$ are each independently selected from the group consisting of hydrogen and $C_1$-$C_6$ alkyl;
  $R^3$, $R^4$, $R^6$, and $R^7$ are each independently selected from the group consisting of hydrogen, $C_1$-$C_6$ alkyl, $C_1$-$C_6$ alkoxy, carboxyl, halogen, and $CF_3$;
  and $R^8$ is selected from the group consisting of —$OR^{15}$ and —$N(R^{16}R^{17})$, wherein $R^{15}$, $R^{16}$, and $R^{17}$ are each independently selected from the group consisting of hydrogen and $C_1$-$C_6$ alkyl.

Alternatively, the compound of Formula I may be a compound of Formula Ib or a salt thereof,

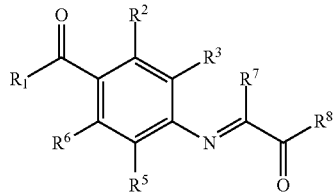

Formula Ib wherein
  $R^1$ is selected from the group consisting of —$OR^9$ and —$N(R^{10}R^{11})$, wherein $R^9$, $R^{10}$, and $R^{11}$ are each independently selected from the group consisting of hydrogen and $C_1$-$C_6$ alkyl;

$R^2$ is selected from the group consisting of —$OR^{12}$ and —$N(R^{13}R^{14})$, wherein $R^{12}$, $R^{13}$, and $R^{14}$ are each independently selected from the group consisting of hydrogen and $C_1$-$C_6$ alkyl;

$R^3$, $R^5$, $R^6$, and $R^7$ are each independently selected from the group consisting of hydrogen, $C_1$-$C_6$ alkyl, $C_1$-$C_6$ alkoxy, carboxyl, halogen, and $CF_3$;

and $R^8$ is selected from the group consisting of —$OR^{15}$ and —$N(R^{16}R^{17})$, wherein $R^{15}$, $R^{16}$, and $R^{17}$ are each independently selected from the group consisting of hydrogen and $C_1$-$C_6$ alkyl.

In some embodiments, the compound is a compound of Formula I, Ia, or Ib wherein $R^1$ is selected from the group consisting of —OH, —$OCH_3$, —$OCH_2CH_3$, —$NH_2$, and —$N(CH_3)_2$. $R^1$ can be selected from the group consisting of —OH, —$OCH_3$, and —$OCH_2CH_3$. For example, $R^1$ can be —OH. Alternatively, $R^1$ can be —$OCH_3$ or —$OCH_2CH_3$. For example, $R^1$ can be —$OCH_2CH_3$.

In some embodiments, the compound is a compound of Formula I, Ia, or Ib wherein $R^2$ is selected from the group consisting of —OH, —$OCH_3$, —$OCH_2CH_3$, —$NH_2$, and —$N(CH_3)_2$. $R^2$ can be selected from the group consisting of —OH, —$OCH_3$, —$OCH_2CH_3$, —$NH_2$, and $N(CH_3)_2$. $R^2$ can be selected from the group consisting of —OH, —$OCH_3$, and —$NH_2$. For example, $R^2$ can be —OH.

In some embodiments, the compound is a compound of Formula I, Ia, or Ib wherein $R^3$, $R^6$, and $R^{11}$ are each independently selected from the group of hydrogen, halogen, —$CH_3$, —$OCH_3$, and —$CF_3$. For example, $R^3$, $R^6$, and $R^{11}$ can each be hydrogen.

In some embodiments, the compound is a compound of Formula I or Ia wherein $R^4$ is selected from the group of hydrogen, halogen, —$CH_3$, —$OCH_3$, and —$CF_3$. For example, $R^4$ can be hydrogen.

In some embodiments, the compound is a compound of Formula I or Ib wherein $R^5$ is selected from the group of hydrogen, halogen, —$CH_3$, —$OCH_3$, and —$CF_3$. For example, $R^5$ can be hydrogen.

In some embodiments, the compound is a compound of Formula I, Ia, or Ib wherein $R^{12}$ is selected from the group consisting of —OH, —$OCH_3$, —$OCH_2CH_3$, —$NH_2$, and —$N(CH_3)_2$. $R^{12}$ can be selected from the group consisting of —OH, —$OCH_3$, and —$OCH_2CH_3$. For example, $R^{12}$ can be —OH. Alternatively, $R^{12}$ can be —$OCH_3$ or —$OCH_2CH_3$. For example, $R^{12}$ can be —$OCH_2CH_3$.

Also provided herein is a compound of Formula II, or a salt thereof,

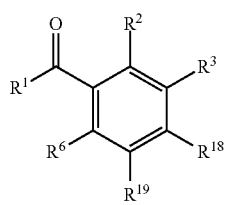

Formula II wherein
$R^1$ is selected from the group consisting of —$OR^9$ and —$N(R^{10}R^{11})$, wherein $R^9$, $R^{10}$, and $R^{11}$ are each independently selected from the group consisting of hydrogen and $C_1$-$C_6$ alkyl;
$R^2$ is selected from the group consisting of —$OR^{12}$ and —$N(R^{13}R^{14})$, wherein $R^{12}$, $R^{13}$, and $R^{14}$ are each independently selected from the group consisting of hydrogen and $C_1$-$C_6$ alkyl;

$R^3$ and $R^6$ are each independently selected from the group consisting of hydrogen, $C_1$-$C_6$ alkyl, $C_1$-$C_6$ alkoxy, carboxyl, halogen, and $CF_3$;

one of $R^{18}$ and $R^{19}$ is selected from the group consisting of hydrogen, $C_1$-$C_6$ alkyl, $C_1$-$C_6$ alkoxy, carboxyl, halogen, and $CF_3$, and the other of $R^{18}$ and $R^{19}$ is a moiety having the following structure:

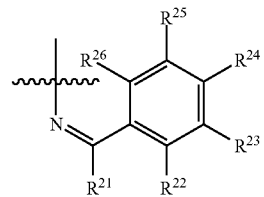

wherein
$R^{21}$, $R^{22}$, $R^{25}$, and $R^{26}$ are each independently selected from the group consisting of hydrogen, $C_1$-$C_6$ alkyl, $C_1$-$C_6$ alkoxy, carboxyl, halogen, and $CF_3$;

$R^{23}$ is selected from the group consisting —$OR^{27}$ and —$N(R^{28}R^{29})$, wherein $R^{27}$, $R^{28}$, and $R^{29}$ are each independently selected from the group consisting of hydrogen and $C_1$-$C_6$ alkyl;

and $R^{24}$ is selected from the group consisting of —$OR^{30}$ and —$N(R^{31}R^{32})$, wherein $R^{30}$, $R^{31}$, and $R^{32}$ are each independently selected from the group consisting of hydrogen and $C_1$-$C_6$ alkyl.

For example, the compound of Formula II may be a compound of Formula IIa or a salt thereof,

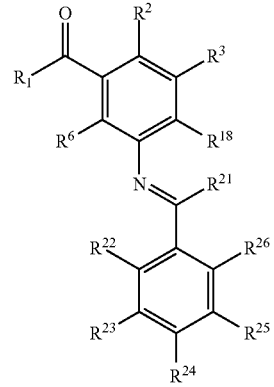

Formula IIa wherein
$R^1$ is selected from the group consisting of —$OR^9$ and —$N(R^{10}R^{11})$, wherein $R^9$, $R^{10}$, and $R^{11}$ are each independently selected from the group consisting of hydrogen and $C_1$-$C_6$ alkyl;
$R^2$ is selected from the group consisting of —$OR^{12}$ and —$N(R^{13}R^{14})$, wherein $R^{12}$, $R^{13}$, and $R^{14}$ are each independently selected from the group consisting of hydrogen and $C_1$-$C_6$ alkyl;
$R^3$, $R^6$, $R^{18}$, $R^{21}$, $R^{22}$, $R^{25}$, and $R^{26}$ are each independently selected from the group consisting of hydrogen, $C_1$-$C_6$ alkyl, $C_1$-$C_6$ alkoxy, carboxyl, halogen, and $CF_3$;
$R^{23}$ is selected from the group consisting —$OR^{27}$ and —$N(R^{28}R^{29})$, wherein $R^{27}$, $R^{28}$, and $R^{29}$ are each independently selected from the group consisting of hydrogen and $C_1$-$C_6$ alkyl;

and R²⁴ is selected from the group consisting of —OR³⁰ and —N(R³¹R³²), wherein R³⁰, R³¹, and R³² are each independently selected from the group consisting of hydrogen and C₁-C₆ alkyl.

Alternatively, the compound of Formula II may be a compound of Formula IIb or a salt thereof,

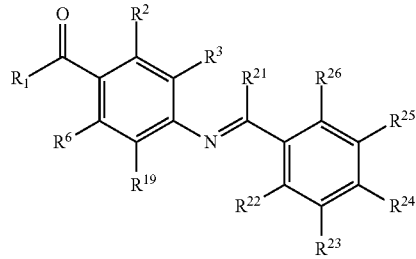

Formula IIb wherein
R¹ is selected from the group consisting of —OR⁹ and —N(R¹⁰R¹¹), wherein R⁹, R¹⁰, and R¹¹ are each independently selected from the group consisting of hydrogen and C₁-C₆ alkyl;
R² is selected from the group consisting of —OR¹² and —N(R¹³R¹⁴), wherein R¹², R¹³, and R¹⁴ are each independently selected from the group consisting of hydrogen and C₁-C₆ alkyl;
R³, R⁶, R¹⁹, R²¹, R²², R²⁵, and R²⁶ are each independently selected from the group consisting of hydrogen, C₁-C₆ alkyl, C₁-C₆ alkoxy, carboxyl, halogen, and CF₃;
R²³ is selected from the group consisting —OR²⁷ and —N(R²⁸R²⁹), wherein R²⁷, R²⁸, and R²⁹ are each independently selected from the group consisting of hydrogen and C₁-C₆ alkyl;
and R²⁴ is selected from the group consisting of —OR³⁰ and —N(R³¹R³²), wherein R³⁰, R³¹, and R³² are each independently selected from the group consisting of hydrogen and C₁-C₆ alkyl.

In some embodiments, the compound is a compound of Formula II, IIa, or IIb wherein R¹ is selected from the group consisting of —OH, —OCH₃, —OCH₂CH₃, —NH₂, and —N(CH₃)₂. R¹ can be selected from the group consisting of —OH, —OCH₃, and —OCH₂CH₃. For example, R¹ can be —OH. Alternatively, R¹ can be —OCH₃ or —OCH₂CH₃. For example, R¹ can be —OCH₂CH₃.

In some embodiments, the compound is a compound of Formula II, IIa, or IIb wherein R² is selected from the group consisting of —OH, —OCH₃, —OCH₂CH₃, —NH₂, and —N(CH₃)₂. R² can be selected from the group consisting of —OH, —OCH₃, and —NH₂. For example, R² can be —OH.

In some embodiments, the compound is a compound of Formula II, IIa, or IIb wherein R³, R⁶, R²¹, R²², R²⁵, and R²⁶ are each independently selected from the group of hydrogen, halogen, —CH₃, —OCH₃, and —CF₃. For example, R³, R⁶, R²¹, R²², R²⁵, and R²⁶ can each be hydrogen.

In some embodiments, the compound is a compound of Formula II or IIa wherein R¹⁸ is selected from the group of hydrogen, halogen, —CH₃, —OCH₃, and —CF₃. For example, R¹⁸ can be hydrogen.

In some embodiments, the compound is a compound of Formula II or IIb wherein R¹⁹ is selected from the group of hydrogen, halogen, —CH₃, —OCH₃, and —CF₃. For example, R¹⁹ can be hydrogen.

In some embodiments, the compound is a compound of Formula II, IIa, or IIb wherein R²³ is selected from the group consisting of —OH, —OCH₃, —OCH₂CH₃, —NH₂, and —N(CH₃)₂. R²³ can be selected from the group consisting of —OH, —OCH₃, and —NH₂. For example, R²³ can be —OCH₃.

In some embodiments, the compound is a compound of Formula II, IIa, or IIb wherein R²⁴ is selected from the group consisting of —OH, —OCH₃, —OCH₂CH₃, —NH₂, and —N(CH₃)₂. R²⁴ can be selected from the group consisting of —OH, —OCH₃, and —NH₂. For example, R²⁴ can be —OH.

Non-limiting examples of species include 5-glyoxyliminosalicylic acid of Formula Ia-i, or a salt thereof,

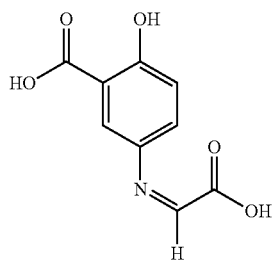

Formula Ia-i ethyl 5-ethylglyoxyliminosalicylate of Formula Ia-ii, or a salt thereof,

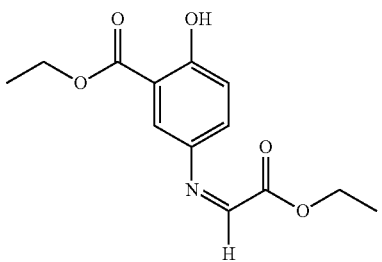

Formula Ia-ii 5-ethylglyoxyliminosalicylic acid of Formula Ia-iii, or a salt thereof,

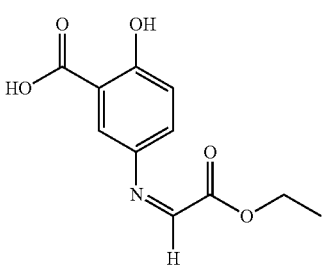

Formula Ia-iii 4-glyoxyliminosalicylic acid of Formula Ib-i, or a salt thereof,

Formula Ib-i

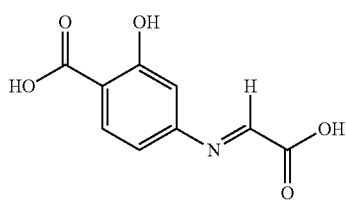

4-ethylgloxyliminosalicylic acid of Formula Ib-ii, or a salt thereof,

Formula Ib-ii

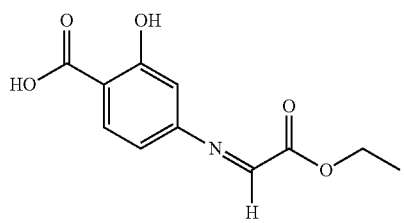

5-vanilliniminosalicylic acid of Formula IIa-i, or a salt thereof,

Formula IIa-i

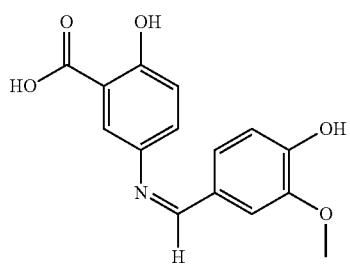

and 4-vanilliniminosalicylic acid of Formula IIb-i, or a salt thereof.

Formula IIb-i

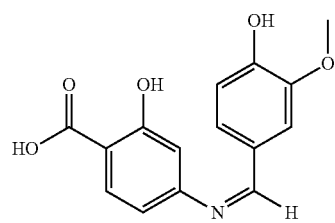

As used herein, the term "hydrogen" includes both stable isotopes of hydrogen, namely $^1$H (also known as protium) and $^2$H (also known as deuterium).

As used herein, the term "halogen" refers to a halogen atom selected from the group consisting of fluorine, chlorine, bromine, and iodine. In preferred embodiments, the halogen is selected from the group consisting of fluorine and chlorine. For example, the halogen can be fluorine.

As used herein, the term "alkoxy" refers to a group of the form —OR', wherein R' is selected from the group consisting of $C_1$-$C_6$ alkyl. For example, the group —OCH$_3$ may be referred to herein as "methoxy." The group —OCH$_2$CH$_3$ may be referred to herein as "ethoxy."

As used herein, the term "carboxyl" refers to a group of the form —C(O)OH.

Pharmaceutical Compositions

Also provided herein is a pharmaceutical composition comprising a compound of Formula I or Formula II as described herein.

Generally, the pharmaceutical composition may comprise one or more compounds as described herein. For example, the composition may comprise two or more compounds as described herein.

The pharmaceutical composition can comprise one or more pharmaceutically acceptable excipients. Suitable excipients are generally known to those skilled in the art.

The pharmaceutical composition can generally comprise any dosage form known in the art. For example, the composition can be in the form of a tablet, capsule, granulated powder, or gel. As further non-limiting examples, the composition can be in the form of a liquid suspension, emulsion, or aqueous solution.

As a non-limiting example, the compounds described herein may be incorporated into a soluble enema formulation. Without being bound to a particular theory, it is believed that one or more of the compounds described herein are stable when dissolved in a phosphate buffer, and particularly so in the absence of chloride anions. Accordingly, the compounds described herein may be incorporated into a stable, soluble enema formulation wherein the compound is dissolved in a phosphate buffer.

Methods of Treatment

Also provided herein is a method of treating an intestinal inflammatory disorder in a human. Generally, the method comprises administering a pharmaceutical composition as described herein (i.e., a composition comprising a compound of Formula I or Formula II) to a human having an intestinal inflammatory disorder.

Because the compounds described herein are prodrugs for mesalazine, they are generally useful to treat the same disorders and conditions for which mesalazine is indicated. As non-limiting examples, the compounds described herein may be used to treat intestinal inflammatory disorders selected from the group consisting of Crohn's disease, inflammatory bowel disease ("IBS"), and ulcerative colitis.

Other objects and features will be in part apparent and in part pointed out hereinafter.

EXAMPLES

The following non-limiting examples are provided to further illustrate the present disclosure.

Example 1: Synthesis of 5-Glyoxyliminosalicylic Acid (Formula Ia-i)

In a 50 ml round-bottomed flask, 1.5 g of 5-aminosalicylic acid ("5-ASA"), 2.0 g of glyoxylic acid monohydrate and 1.5 g of 3 Å molecular sieves (8-12 mesh) were suspended in 20 ml of methanol. This suspension was stirred magnetically in a 40° C. water bath. The reaction mixture was maintained at 40° C. for 2 hours, then allowed to cool to room temperature and stirred overnight.

The reaction mixture was checked for completion by mass spectrometry (infusion in methanol), and no starting material (5-ASA 152 amu–m/z) was present. The reaction mixture was a deep yellow solution. The mixture was passed through filter paper under vacuum to remove the molecular sieves. The sieves were washed with 5 ml of methanol. The filtrate was concentrated to dryness under a stream of nitrogen resulting in an oily granular semi-solid. The oily granular semi-solid was triturated with 20 ml of acetone causing the material to solidify.

The solid was isolated by filtration and washed with 5 ml of acetone. The isolated solid was allowed to dry at room temperature on the funnel. This produced 1.54 g of 5-glyoxyliminosalicylic acid ($M_w$=209.2, $C_9H_7O_5N$) as an orange solid. MS 208.1 amu (–m/z via infusion). As shown in FIG. 1, the FTIR fingerprint region did not match 5-ASA.

Example 2: In Vitro Testing of 5-Glyoxyliminosalicylic Acid (Formula Ia-i)

12 mg of 5-glyoxyliminosalicylic acid (prepared as described in Example 1 above) and 12 mg of 5-aminosalicylic acid were combined in a scintillation vial with 6 ml buffered saline. The vial was held at ambient temperature for 22.75 hours and sampled. The percentage of 5-aminosalicylic acid increased at this time-point to 87% by HPLC. No other peaks were present.

The same experiment, repeated as described above but in the absence of saline, showed very little mesalamine evolution. Without being bound to a particular theory, it is believed that for 5-glyoxyliminosalicylic acid, the presence of chloride greatly increases the rate of mesalamine evolution.

Example 3: Synthesis of Ethyl 5-Ethylglyoxyliminosalicylate (Formula Ia-ii)

In a 25 ml round-bottomed, 1.9 g of 5-Aminosalicylic acid was suspended in 14 g of ethanol while being stirred magnetically. To the suspended 5-Aminosalicylic acid, 3 g of sulfuric acid was added. The reaction mixture was heated to reflux and soaked for 2 hour. The round-bottomed flask was not stoppered to allow vapor to distill off. Periodically ethanol was added to the reaction mixture when the volume dropped. The reaction mixture was gradually reduced to an oil via reflux.

Distilled water (20 ml) was added to the oil to produce a cloudy suspension. This suspension was pH adjusted using ammonium hydroxide to a pH between 7-8. The cloudy pH-adjusted aqueous suspension was extracted with 30 ml of ethyl acetate in a separatory funnel. The aqueous and ethyl acetate layers were clear and separated distinctly. The lower aqueous layer was separated from the upper ethyl acetate layer. The ethyl acetate layer was dried over sodium sulfate. The ethyl acetate was decanted from the sodium sulfate and concentrated to an oil, 1.6 g of 5-aminosalicylic acid ethyl ester ($M_w$=181.1, $C_9H_{12}O_3N$) on a rotary evaporator. GCMS 182.5 amu (+m/z).

Figure 2:
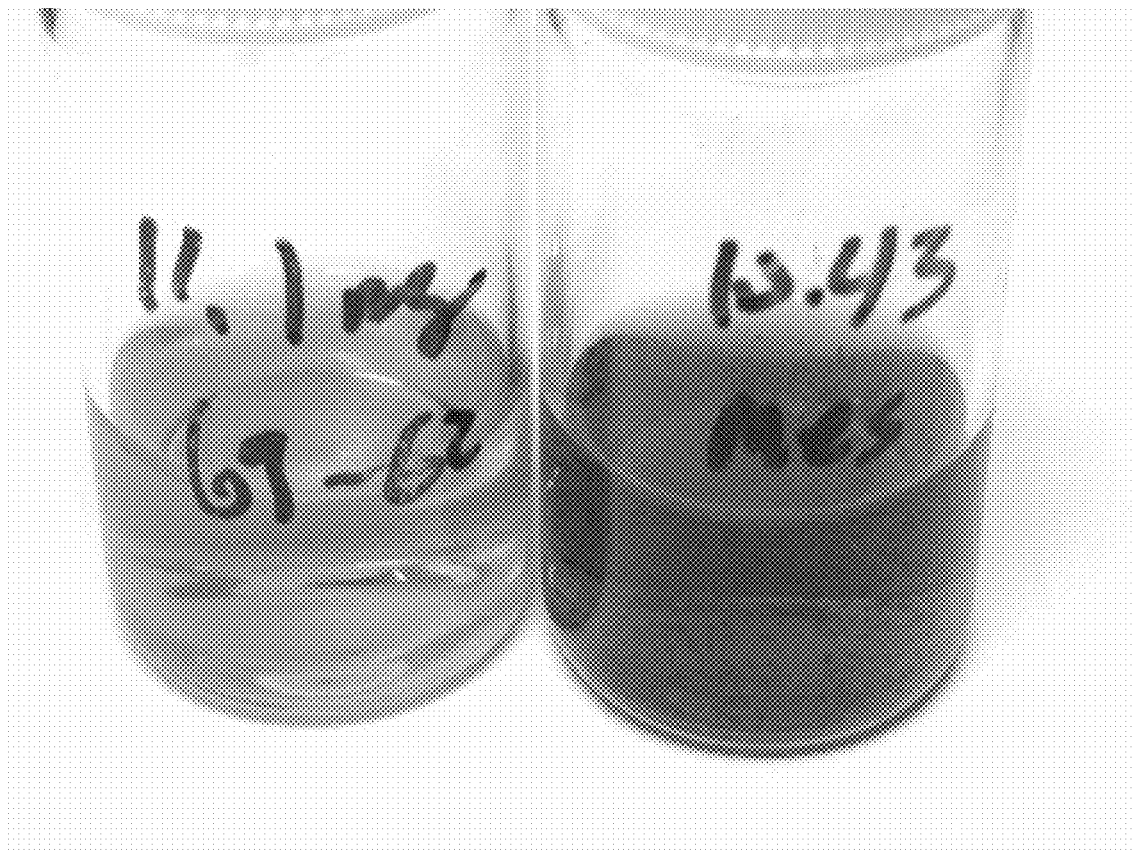
FIG. 2 is a photograph of the same vials shown in FIG. 1, taken after 3 days of storage under ambient conditions as described in Example 11.

In a 10 ml scintillation vial, 0.182 g of 5-aminosalicylic acid ethyl ester, 0.2 g of ethyl glyoxylate, 50% solution in toluene and 2 ml of toluene were combined. The reaction mixture was stirred magnetically and heated to reflux. The scintillation vial remained open to allow the water vapor to reflux off to drive the reaction. The reaction mixture was refluxed for only 5 minutes and was approximately 90% complete by GC/MS. The reaction mixture was maintained at reflux for a total of 1 hour. Portions of toluene were added periodically to maintain the reaction mixture volume. After the 1 hour reaction period, the volume of the reaction mixture was reduced by allowing the toluene to distill off to produce an oil. The oil was dried further to a crystalline solid by reducing volume under a stream of nitrogen. The resulting solid was further dried in a vacuum oven at 60° C. This produced 0.29 g of ethyl 5-ethylglyoxyliminosalicylate ($M_w$=265.2, $C_{13}H_{15}O_5N$, Theoretical yield=0.27 g) as a yellow crystalline solid. GCMS 265.8 amu (+m/z). As shown in FIG. 2, the FTIR fingerprint region did not match 5-ASA.

Example 4: Synthesis of 5-Ethylglyoxyliminosalicylic Acid (Formula Ia-iii)

In a scintillation vial, 0.153 g of 5-Aminosalicylic acid was charged along with 0.2 ml (0.2 g) of ethyl glyoxylate, 50% solution in toluene. The reaction mixture was further diluted with 2 ml of toluene and stirred magnetically to properly mix. The reaction mixture was heated to reflux and maintained for 10 minutes. A dark oil formed along the walls of the scintillation vial as the reaction progressed. The resulting orange solution was decanted while hot from the dark oil into another scintillation vial. As the orange solution cooled, crystals began to form. The crystals were isolated by filtration and allowed to air dry. This produced 0.18 g of 5-ethylglyoxyliminosalicylic acid ($M_w$=237.1, Theoretical yield=0.236 g) as a crystalline orange solid. MS 235.9 amu (–m/z via infusion). No 5-ASA was present. As shown in FIG. 3, the FTIR fingerprint region did not match 5-ASA.

Example 5: In Vitro Testing of of 5-Ethylglyoxyliminosalicylic acid (Formula Ia-iii)

10 mg of 5-ethylglyoxyliminosalicylic acid (prepared as described in Example 4 above) was stored in 10 ml phosphate buffer (pH 6.5) overnight. Infusion of the resulting solution showed the sample had partially decomposed to release 5-ASA. LCMS analysis of the solution showed the sample substantially decomposed to 5-ASA (~90%) based on single ion monitoring of 5-ASA (–m/z 152 amu) and the ester (–m/z 236 amu).

Example 6: Synthesis of 5-Vanilliniminosalicylic Acid (Formula IIa-i)

0.3 g of 5-ASA and 0.3 g vanillin were refluxed in methanol for 1 hour. The mixture initially dissolved, then re-precipitated a dense, bright orange solid. The solids were isolated by filtration, yielding 0.37 g of 5-vanilliniminosalicylic acid ($M_w$=287.29, $C_{15}H_{13}O_5N$) as a bright orange solid. MS 285.6 amu (–m/z via infusion). As shown in FIG. 4, the FTIR fingerprint region did not match 5-ASA.

Example 7: Synthesis of 4-Glyoxyliminosalicylic Acid (Formula Ib-i)

4-Aminosalicylic acid (2.0 g) was charged to a 100 ml round-bottomed flask. Glyoxylic acid monohydrate (2.4 g) was added to the flask. The solids were suspended in 40 ml of dioxane, and molecular sieves (2.0 g, 8-12 mesh, 3 Å) were added. The reaction mixture was heated to 40° C. and held for 3.5 hours. All the solids dissolved to produce a slight yellow/tan solution.

The reaction mixture was passed through filter paper to remove the molecular sieves. The clear yellow dioxane filtrate was concentrated to dryness using a rotary evaporator to produce an oil. The oil was dissolved in 25 ml of ethyl acetate and transferred to a larger tared 250 ml round-bottomed flask. The solution was concentrated to dryness on the rotary evaporator to produce a yellow foam. The temperature of the rotovap bath was raised to 70° C., to ensure that the foam dried and solidified, and soaked under vacuum for 30-45 min. This produced 3.4 g (2.7 g theoretical yield) of 4-Glyoxyliminosalicylic acid as an orange-yellow solidified foam. The isolated 4-Glyoxyliminosalicylic acid was dried in a vacuum oven at 60° C. for 24 hours to give 3.2 g of the isolated solid.

The 3.2 g of crude 4-Glyoxyliminosalicylic acid was dissolved in 150 ml of ethyl acetate, then washed with pH-adjusted distilled water (pH adjusted to 2 with conc. HCl), 2×50 ml, in a separatory funnel. The combined aqueous layers were extracted again with 25 ml of ethyl acetate. The yellow ethyl acetate layer was dried over 15 g of sodium sulfate for 30 min. The ethyl acetate was then concentrated to dryness in a 250 ml round-bottomed flask using a rotary evaporator. This produced a yellow amber oil that eventually formed a solid yellow foam. The solid was scraped from the round-bottomed flask into a tared crystallizing dish and dried at 60° C. for 17 hours under vacuum. This produced 2.8 g (3.1 g theoretical yield, 90% yield) of 4-Glyoxyliminosalicylic acid ($C_9H_7O_5N$, $M_w$=209.16) as a yellow solid. MS 208.0 amu (-m/z via infusion). As shown in FIG. 5, the FTIR fingerprint region did not match 4-ASA.

Example 8: Synthesis of 4-Ethylgloxyliminosalicylic Acid (Formula Ib-ii)

A round-bottomed flask (100 ml) was set up with a medium stir bar, a heating mantle with a VARIAC, a Dean-Stark trap, a condenser, and a water circulation unit. 4-Aminosalicylic acid (2.0 g) was charged to the flask along with 40 ml of toluene. The suspension was stirred at room temperature and acidified with 10 drops of sulfuric acid. Ethyl glyoxylate, 50% solution in toluene (2.9 ml) was added to the reaction. The Dean-Stark trap was attached and filled with toluene to the arm. The condenser was attached to the top of the Dean-Stark trap and the circulation started. The reaction was warmed to reflux.

The progress of the reaction was checked by a methanol infusion on the mass Spec after 2 hours at reflux. Infusion indicated that there was a portion of 4-Aminosalicylic acid remaining. An additional 0.586 ml (20% of 2.93 ml) of ethyl glyoxylate, 50% solution in toluene, was added to the reaction mixture and heated to reflux for another 2 hours.

The heat was shut off and the reaction mixture was allowed to cool to room temperature. The solid was isolated by filtration and washed with 10 ml of toluene. The filter cake was allowed to dry at room temperature while under vacuum for 20 min. The solid was dried in a vacuum oven at 60° C. for 70 hours. This produced 3.2 g of 4-ethylgloxyliminosalicylic acid as a khaki green powder ($M_w$=237.2, Theoretical yield=3.1 g). MS 238.2 amu (+m/z via infusion). As shown in FIG. 6, the FTIR fingerprint region did not match 4-ASA.

Example 9: Synthesis of 4-Vanilliniminosalicylic Acid (Formula IIb-i)

A round-bottomed flask (100 ml) was set up with a medium stir bar, a heating mantle with a VARIAC, a condenser, and a water circulation unit. 4-Aminosalicylic acid (2.0 g) was charged to the flask along with 1.99 g of vanillin. Methanol (40 ml) of methanol was added to the flask. Almost all the solids dissolved quickly at room temperature to form a yellow solution. The reaction mixture was heated to reflux and maintained for approximately 2 hours.

The clear yellowish orange reaction mixture was cooled to room temperature and concentrated to dryness on a rotary evaporator. This produced an orange residue that became a foamy solid after 30 minutes under vacuum at 60° C. The solid was collected, yielding 3.76 g of 4-vanilliniminosalicylic acid ($M_w$=287.3, $C_{15}H_{13}O_5N$, Theoretical yield=3.75 g) as a copper -orange solid. MS 286.1 amu (+m/z via infusion). As shown in FIG. 7, the FTIR fingerprint region did not match 4-ASA.

Example 10: Solubility Testing

Compounds of Formulas I and II, prepared as described in the examples above, were tested to determine their solubility in a sodium phosphate buffer. For the purpose of comparison, the solubility of mesalazine in the sodium phosphate buffer was also evaluated.

An aqueous buffer solution comprising 0.02 molar dibasic sodium phosphate was prepared. A weighted amount of solid was sonicated in the buffer, and then centrifuged to collect the undissolved material. The undissolved solid was dried in vacuuo and weighed. The mass of the undissolved portion was then used to calculate the mass that was successfully dissolved in the known volume of buffer.

The solubility values obtained using this procedure are set forth in Table 1 below.

TABLE 1

| | Solubility Data | |
|---|---|---|
| Formula | Compound | Solubility (mg/ml) |
| — | Mesalazine | 5.24 |
| Ia-i | 5-glyoxyliminosalicylic acid | 11.00 |
| Ia-ii | ethyl 5-ethylglyoxyliminosalicylate | 0.13 |
| Ia-iii | 5-ethylglyoxyliminosalicylic acid | 12.00 |
| Ib-i | 4-glyoxyliminosalicylic acid | 17.34 |
| Ib-ii | 4-ethylgloxyliminosalicylic acid | 10.19 |
| IIa-i | 5-vanilliniminosalicylic acid and | 3.45 |
| IIb-i | 4-vanilliniminosalicylic acid | 7.35 |

Example 11: Solution Stability

An aqueous buffer solution comprising 0.02 molar dibasic sodium phosphate was prepared. An 11 mg sample of 5-glyoxyliminosalicylic acid (Formula Ia-i) was added to a vial containing 5 ml of the buffer solution. For comparison, an 11 mg sample of mesalazine was added to an identical vial with 5 ml of the buffer solution. Both vials were stored at ambient temperature.

An initial photograph of the vials is shown in FIG. 1. The vial on the left contains the dissolved 5-glyoxyliminosalicylic acid, while the vial on the right contains the dissolved mesalazine. A second photograph taken after 3 days of storage is shown in FIG. 2. As shown in the image, the mesalazine solution turned a dark brown color, and a significant amount of brown solid material precipitated. The 5-glyoxyliminosalicylic acid solution, in contrast, was still clear and lightly colored. This indicates that 5-glyoxyliminosalicylic acid, when dissolved in an aqueous sodium phosphate buffer, exhibits a significantly greater degree of storage stability than mesalazine.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description shall be interpreted as illustrative and not in a limiting sense.

What is claimed is:

1. A compound of Formula I, or a salt thereof,

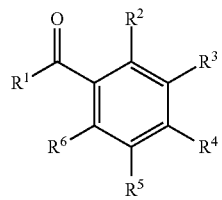

wherein
- $R^1$ is selected from the group consisting of —$OR^9$ and —$N(R^{10}R^{11})$, wherein $R^9$, $R^{10}$, and $R^{11}$ are each independently selected from the group consisting of hydrogen and $C_1$-$C_6$ alkyl;
- $R^2$ is selected from the group consisting of —$OR^{12}$ and —$N(R^{13}R^{14})$, wherein $R^{12}$, $R^{13}$, and $R^{14}$ are each independently selected from the group consisting of hydrogen and $C_1$-$C_6$ alkyl;
- $R^3$ and $R^6$ are each independently selected from the group consisting of hydrogen, $C_1$-$C_6$ alkyl, $C_1$-$C_6$ alkoxy, carboxyl, halogen, and $CF_3$;
- one of $R^4$ and $R^5$ is selected from the group consisting of hydrogen and $C_1$-$C_6$ alkyl, and the other of $R^4$ and $R^5$ is a moiety having the following structure:

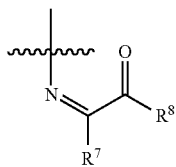

wherein $R^7$ is selected from the group consisting of hydrogen, $C_1$-$C_6$ alkyl, $C_1$-$C_6$ alkoxy, carboxyl, halogen, and $CF_3$;
and $R^8$ is selected from the group consisting of —$OR^{15}$ and —$N(R^{16}R^{17})$, wherein $R^{15}$, $R^{16}$, and $R^{17}$ are each independently selected from the group consisting of hydrogen and $C_1$-$C_6$ alkyl.

2. The compound of claim 1 wherein the compound is of Formula Ia, or a salt thereof,

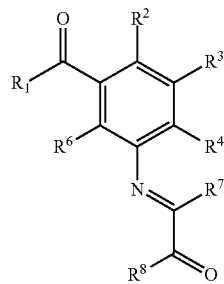

wherein
- $R^1$ is selected from the group consisting of —$OR^9$ and —$N(R^{10}R^{11})$, wherein $R^9$, $R^{10}$, and $R^{11}$ are each independently selected from the group consisting of hydrogen and $C_1$-$C_6$ alkyl;
- $R^2$ is selected from the group consisting of —$OR^{12}$ and —$N(R^{13}R^{14})$, wherein $R^{12}$, $R^{13}$, and $R^{14}$ are each independently selected from the group consisting of hydrogen and $C_1$-$C_6$ alkyl;
- $R^3$, $R^4$, $R^6$, and $R^7$ are each independently selected from the group consisting of hydrogen, $C_1$-$C_6$ alkyl, $C_1$-$C_6$ alkoxy, carboxyl, halogen, and $CF_3$;
- and $R^8$ is selected from the group consisting of —$OR^{15}$ and —$N(R^{16}R^{17})$, wherein $R^{15}$, $R^{16}$, and $R^{17}$ are each independently selected from the group consisting of hydrogen and $C_1$-$C_6$ alkyl.

3. The compound of claim 2 wherein $R^4$ is selected from the group consisting of hydrogen, halogen, —$CH_3$, —$OCH_3$, and —$CF_3$.

4. The compound of claim 3 wherein $R^4$ is hydrogen.

5. The compound of claim 1 wherein the compound is of Formula Ib, or a salt thereof,

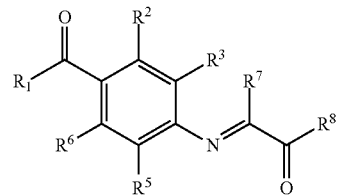

wherein
- $R^1$ is selected from the group consisting of —$OR^9$ and —$N(R^{10}R^{11})$, wherein $R^9$, $R^{10}$, and $R^{11}$ are each independently selected from the group consisting of hydrogen and $C_1$-$C_6$ alkyl;
- $R^2$ is selected from the group consisting of —$OR^{12}$ and —$N(R^{13}R^{14})$, wherein $R^{12}$, $R^{13}$, and $R^{14}$ are each independently selected from the group consisting of hydrogen and $C_1$-$C_6$ alkyl;
- $R^3$, $R^5$, $R^6$, and $R^7$ are each independently selected from the group consisting of hydrogen, $C_1$-$C_6$ alkyl, $C_1$-$C_6$ alkoxy, carboxyl, halogen, and $CF_3$;
- and $R^8$ is selected from the group consisting of —$OR^{15}$ and —$N(R^{16}R^{17})$, wherein $R^{15}$, $R^{16}$, and $R^{17}$ are each independently selected from the group consisting of hydrogen and $C_1$-$C_6$ alkyl.

6. The compound of claim 5 wherein $R^5$ is selected from the group consisting of hydrogen, halogen, —$CH_3$, —$OCH_3$, and —$CF_3$.

7. The compound of claim 6 wherein $R^5$ is hydrogen.

8. The compound of claim 1 wherein $R^1$ is selected from the group consisting of —OH, —OCH$_3$, —OCH$_2$CH$_3$, —NH$_2$, and —N(CH$_3$)$_2$.

9. The compound of claim 8 wherein $R^1$ is selected from the group consisting of —OH, —OCH$_3$, and —OCH$_2$CH$_3$.

10. The compound of claim 9 wherein $R^1$ is —OH.

11. The compound of claim 9 wherein $R^1$ is —OCH$_2$CH$_3$.

12. The compound of claim 1 wherein $R^2$ is selected from the group consisting of —OH, —OCH$_3$, —OCH$_2$CH$_3$, —NH$_2$, and —N(CH$_3$)$_2$.

13. The compound of claim 12 wherein $R^2$ is selected from the group consisting of —OH, —OCH$_3$, and —NH$_2$.

14. The compound of claim 13 wherein $R^2$ is —OH.

15. The compound of claim 1 wherein $R^3$, $R^6$, and $R^7$ are each independently selected from the group consisting of hydrogen, halogen, —CH$_3$, —OCH$_3$, and —CF$_3$.

16. The compound of claim 15 wherein each of $R^3$, $R^6$, and $R^7$ is hydrogen.

17. The compound of claim 1 wherein $R^8$ is selected from the group consisting of —OH, —OCH$_3$, —OCH$_2$CH$_3$, —NH$_2$, and —N(CH$_3$)$_2$.

18. The compound of claim 17 wherein $R^8$ is selected from the group consisting of —OH, —OCH$_3$, and —OCH$_2$CH$_3$.

19. The compound of claim 18 wherein $R^8$ is —OH.

20. A compound of claim 1 selected from the group consisting of:

5-glyoxyliminosalicylic acid, or a salt thereof;
ethyl 5-ethylglyoxyliminosalicylate, or a salt thereof;
5-ethylglyoxyliminosalicylic acid, or a salt thereof;
4-glyoxyliminosalicylic acid, or a salt thereof; and
4-ethylgloxyliminosalicylic acid, or a salt thereof.

21. A pharmaceutical composition comprising a compound as set forth in claim 1 and at least one pharmaceutically acceptable excipient.

22. A pharmaceutical composition comprising a compound as set forth in claim 20 and at least one pharmaceutically acceptable excipient.

23. The pharmaceutical composition of claim 21 wherein the composition is in the form of a suppository, tablet, capsule, granulated powder, or gel.

24. The pharmaceutical composition of claim 21 wherein the composition is in the form of a liquid suspension, emulsion, or aqueous solution.

25. The pharmaceutical composition of claim 21 wherein the composition is a soluble enema formulation.

26. The pharmaceutical composition of claim 21 wherein the compound is dissolved in a phosphate buffer.

27. The pharmaceutical composition of claim 26 wherein the composition is a soluble enema formulation wherein the compound is dissolved in a phosphate buffer.

* * * * *